(12) United States Patent
Celi de la Torre et al.

(10) Patent No.: US 8,183,522 B2
(45) Date of Patent: May 22, 2012

(54) HIGH FILLING FLOW WATER PHANTOM

(75) Inventors: Juan-Carlos Celi de la Torre, Heidelberg (DE); Stefan Reinhold, Nürnberg (DE); Roman Harmansa, Burgthann/Mimberg (DE); Rob Plompen, Nürnberg (DE)

(73) Assignee: Ion Beam Applications S.A., Louvain-la-Neuve (BE)

( * ) Notice: Subject to any disclaimer, the term of this patent is extended or adjusted under 35 U.S.C. 154(b) by 485 days.

(21) Appl. No.: 12/507,518

(22) Filed: Jul. 22, 2009

(65) Prior Publication Data

US 2010/0019137 A1    Jan. 28, 2010

(30) Foreign Application Priority Data

Jul. 22, 2008 (EP) .................................. 08160916

(51) Int. Cl.
*G01D 18/00* (2006.01)
*G01T 1/16* (2006.01)
(52) U.S. Cl. ...................................... 250/252.1; 378/207
(58) Field of Classification Search .............. 250/252.1, 250/393.06; 378/207
See application file for complete search history.

(56) References Cited

U.S. PATENT DOCUMENTS

| 7,193,220 B1 * | 3/2007 | Navarro | 250/374 |
| 2003/0045803 A1 * | 3/2003 | Acharya | 600/508 |

FOREIGN PATENT DOCUMENTS

| EP | 1 852 714 A1 | 11/2007 |
| FR | 2723212 A1 * | 2/1996 |
| WO | 2007/081662 A2 | 7/2007 |

* cited by examiner

*Primary Examiner* — David Porta
*Assistant Examiner* — Casey Bryant
(74) *Attorney, Agent, or Firm* — Fitch, Even, Tabin & Flannery, LLP

(57) ABSTRACT

The present invention is related to a water phantom for measuring and determining the dose distribution of radiation produced by a particle beam or photon radiation beam comprising: a water tank, the water tank having a lower base and side walls; supply means for supplying water to the water tank. The water tank comprises an intermediate base that forms, together with side walls and said lower base, a closed lower tank underneath said intermediate base and an upper tank above said intermediate base, the closed lower tank being connected to the supply means and allowing the flow of water toward said upper tank through a plurality of water admission passages defined in the intermediate base to provide an unturbulent water flow within said water tank 2.

8 Claims, 6 Drawing Sheets

HIGH FILLING FLOW WATER PHANTOM

FIELD

The present invention relates to a water phantom for measuring and verifying the dose distribution of a photon radiation beam or particle beam generated by a radiation therapy apparatus.

BACKGROUND AND STATE OF THE ART

Water phantoms are well known in the art and are typically used for establishing the effect of ionizing radiations over the human body. Such a water phantom mainly comprises a water tank (with a volume of about 250 liters), and is equipped with driving unit which moves a radiation detector (e.g. a watertight air ion chamber probe, a diode or an array of sensors) within the water tank volume into a plurality of measuring positions. The water tank is filled and emptied by means of a pump control mechanism from an external water reservoir.

A well known water phantom is, for example, the "Blue Phantom" manufactured by the assignee of this application, Ion Beam Applications S.A. Louvain-La-Neuve, Belgium. In such a water phantom, the detector may be a single sensor which is progressively positioned in a plurality of measurement positions until a full profile of the radiation beam has been obtained. The "Blue Phantom" may also be equipped with a linear array of detectors which can be moved in two dimensions in the water tank, in order to build a three dimensional map of the radiation field. One example of such an array of detectors is a linear diode array, available as the LDA-99 from Ion Beam Applications S.A. The LDA-99 comprises 99 diodes with 5 mm spacing.

According to known practice, measurements of radiation fields can be performed in two different configurations. In the first configuration known as TPR (tissue to phantom ratio) or SDD (source detector distance) configuration, the source-to-detector distance is fixed as the source-to-water-surface distance varies; and hence, the measurement depth varies during the measurement. The TPR or SDD configuration requires that the water phantom be equipped with a filling level sensor and a bi-directional pumping control allowing adjustment of the water level. In the second configuration known as DD (depth dose) or SSD (source to surface distance) configuration, the source-to-water-surface distance (i.e. the water level) is kept constant as the source-to-detector distance varies. Both configurations (TPR and SSD) are typical and complementary applications during radiotherapy unit commissioning and quality assurance (QA).

WO2007128087 A2, filed by Ion Beam Applications, S.A., describes a water phantom which mainly comprises: a water tank; means for varying the water level in the water tank; and an acquisition detector. According to the '087 PCT publication, the acquisition detector is a two dimensional detector comprising a plurality of sensors and capable of simultaneously measuring the dose in a plurality of points in an area. This acquisition detector is located beneath the water tank in a fixed position with respect to the water tank and opposite to the beam. Subsequent measurements are performed by varying each time the water level within the water tank, until the dose distribution in the entire volume of the water tank is obtained. The '087 publication describes the water phantom as capable of performing measurement in both TPR and SSD configurations.

Though the use of water phantoms has been an established standard since many years, the handling of these large scanning water phantoms is cumbersome and time consuming partly because of the long filling and emptying time of the water tank.

During the preparation of water phantom measurements, the water tank, the sensor moving mechanics, and the water surface have to be thoroughly aligned with respect to the radiation field. It is evident that in order to setup the water phantom accurately, the water surface has to be as calm as possible so that one can properly position the detector with respect to the water surface in order to get well aligned scans (typical accuracy required for the detector-to-water depth is about 0.5 mm). On the other hand, since the source-to-water-surface distance is an important measurement parameter, it is also important to have a calm water surface in order to setup the source-to-water-surface distance accurately. That is why conventional water phantoms, with typical water flow rates of the incoming water into the water tank of about 20 l/min, are subjected to water waves during the filling process. The presence of such water waves is actually a problem for the setup of the water phantom since they make the water surface very turbulent for quite a while even after filling the tank. Consequently, conventional water phantoms require additional time before one can start measurements waiting for the water within the tank to calm down.

This drawback is even aggravated when performing measurements in TPR configuration wherein the water level is changed during the measurement. In fact, conventional water phantoms require that the flow rate of the incoming water into the water tank is kept low since a high flow rate would create waves within the tank and make the water very turbulent thereby leading to noisy and inaccurate TPR measurements. It is therefore desirable to have a filling and emptying mechanism for the water tank that allows for higher water flow rates while at the same time minimizing the perturbing effects of water waves and turbulences.

The present invention aims to provide a water phantom that overcomes all above-discussed drawbacks of prior art.

More particularly, the present invention aims to provide a water phantom that allows performing a much faster setup as well as faster measurements with respect to prior art, especially in case of TPR configuration.

SUMMARY

A water phantom which measures and determines the dose distribution of radiation produced by a particle beam or photon radiation beam is described herein.

The water phantom comprises: a water tank having a lower base and side walls; and a water supply unit which supplies water to the water tank. The water tank comprises an intermediate or upper base that forms, together with side walls and the lower base, a closed lower tank underneath the intermediate base and an upper tank above the intermediate or upper base. The closed lower tank is connected to the supply unit and allowing the flow of water toward said upper tank through a plurality of water admission passages defined in the intermediate base. These water admission passages are effective and are configured to provide an unturbulent water flow within said water tank at least during the filling of the upper tank.

Preferably, the water phantom further comprises an acquisition detector adapted to be moved along the X-, Y-, Z-axes within the upper tank with a drive unit. This means that the detector can resolve all kind of interpolations between the plot of the function representing the speed of acquisition and the amplitude of beam intensity.

Optionally, the intermediate or upper base further comprises a two dimensional detector comprising a plurality of sensors located in between the water admission passages. These sensors are capable of and are configured to simultaneously measure the dose distribution at a plurality of points in an area. Preferably, the plurality of sensors are located in between and just outside the water admission passage areas. The sensors can be located in the thickness between the upper and lower surface of the intermediate base or can be applied on the upper surface of the intermediate base.

Preferably, the sensors are selected from the group consisting of ionization chambers, diodes, diode, ionization chamber arrays and combinations thereof.

Advantageously, the lower base has a slanted shape so as to create an inclined portion within the closed lower tank correspondingly to the connection with the water supply unit. The slanted shape is configured to allow the evacuation of all unwanted water from the water tank.

In another aspect, a method of measuring and determining the dose distribution of a radiation produced by a particle beam or photon radiation beam using the above described water phantom is described herein. In an important aspect the method includes a method for making commissioning tests of a radiation therapy apparatus. The new commissioning method provides drastically reduced commissioning times compared to commissioning times for known water phantoms.

The water phantom may be preferably used for performing fast TRP measurements of a radiation therapy apparatus.

SHORT DESCRIPTION OF THE DRAWINGS

DETAILED DESCRIPTION

Figure 1:
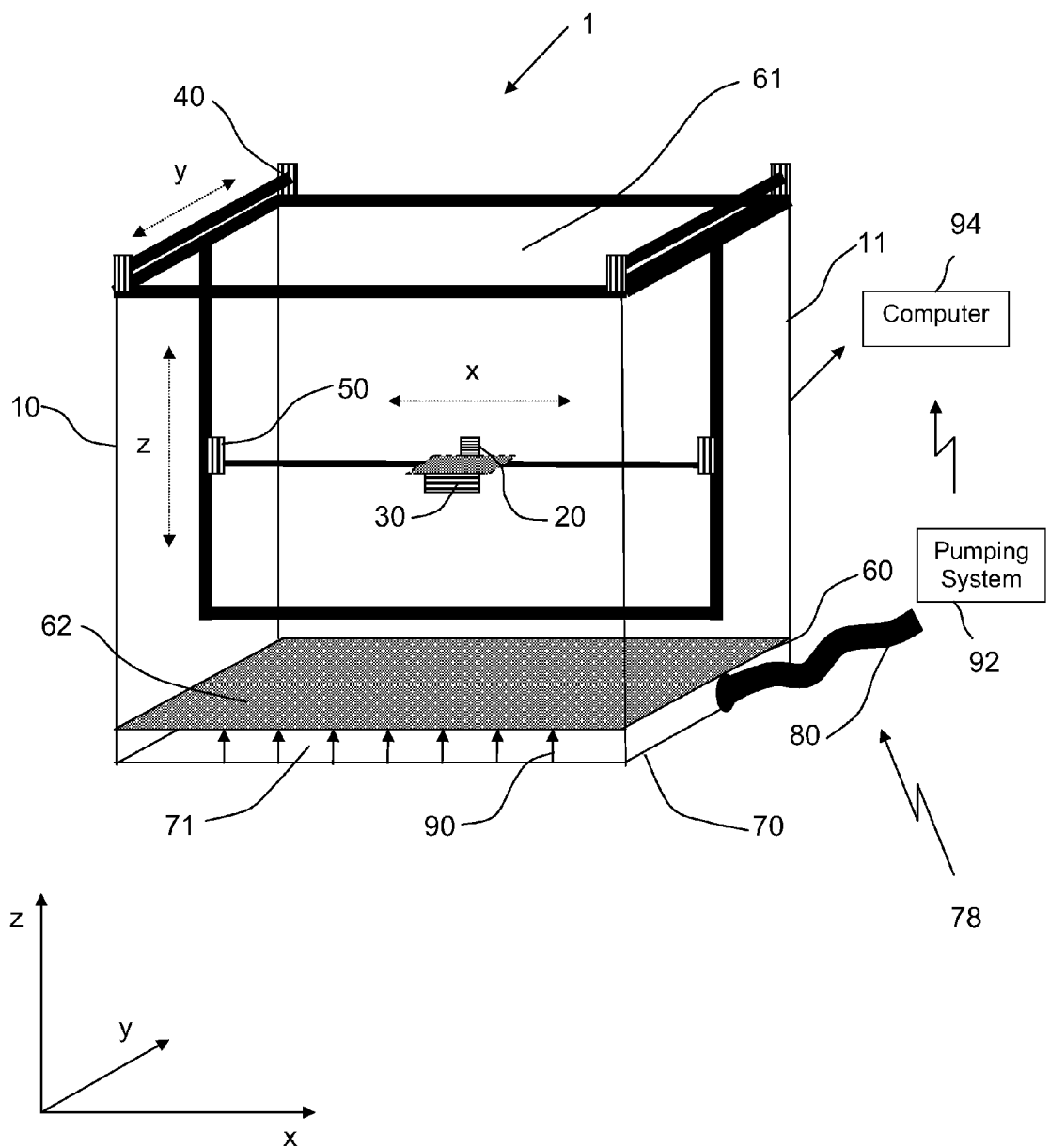
FIG. 1 is a perspective view illustrating a water phantom according to a first embodiment of the present invention.

FIG. 1 is a perspective view of a water phantom. The water phantom 1 mainly comprises a water tank 10, an acquisition detector 20, driving units 30, 40, 50 for moving the acquisition detector 20 within the water tank 10 along X, Y, Z axis respectively. The water tank 10 comprises side walls 11, an upper base 60 and a lower base 70 so as to form a sort of double bottom. The upper base 60 forms together with side walls 11 an upper tank 61 wherein the acquisition detector 20 is configured to be moved by driving units 30, 40 and 50. The lower base 70 cooperates with side walls 11 and the upper base 60 of the water tank 10 in such a manner that it defines a lower closed tank 71 which is located underneath the upper tank 61. The lower closed tank 71 is connected to a water supply system 78 which includes a connection pipe 80 to a high rate pumping system 92 configured to fill empty space within the closed tank 71 with water from a water source. The upper base 60 comprises a matrix of openings 62 arranged on its surface, through which water, flows by virtue of the high rate pumping system. The matrix and pumping system are configured to move water from the lower closed tank 71 upwardly toward and into the upper tank 61, as indicated by arrows 90. The opening matrix comprises 196 openings 62 arranged in 14 rows and 14 columns. Each of the openings 62 has a diameter of 5 mm. However, it is evident that the number, the arrangement and the diameter of these openings 62 may vary depending on the particular application without departing from the invention. Since water flows into and within the upper tank 61 through openings 62 of the lower closed tank 71, it is possible to fill the upper tank 61 without creating unwanted waves even in case of a flow rate of 40 l/min and more, without requiring long times for the water surface to calm.

The water phantom 1 is further provided with read-out circuits (not shown) whose read-out values are processed by a host processing computer 94 which controls the position of the acquisition detector 20 as well as the pumping system for adjusting the water level within the water tank 10. Accordingly, the water phantom is also provided with a water level sensor 96 configured to measure the level of water within the water tank 10.

According to a preferred embodiment, TPR type dose measurements are performed as follows: once the water phantom 1 has been positioned and filled up to the required level by the pumping system, measurements are performed by the acquisition detector 20 fixed in a stationary position within the water tank 10 while the water level in the water tank 10 is continuously adjusted to different subsequent values by moving water from the lower tank to the upper tank. The water should be kept calm when filling the water tank 10 as well as when emptying the water tank. During these measurements, the collected data (dose measurement values and the water level) are processed by the read-out circuits. The above described measurements continue until the desired TPR scans are complete.

Since openings 62 allow the water surface within the water tank 10 to remain unturbulent during the filling process of the water tank 10, it is possible to quickly setup the water phantom 1 and consequently to instantly perform measurements in TPR configuration in a much faster manner compared to the prior art and previously known methods.

Though the water phantom according to this embodiment is particularly suitable for performing measurements in TPR configuration, it should be noticed that it may also be advantageously used for performing measurements in subsequent SSD configurations wherein the source-to-detector-surface is varied for each measurement. SSD type dose measurements are performed as follows: the source-to-water-surface distance is kept constant as the source-to-detector distance varies by moving the acquisition detector 20 within the water tank 10 driving units 30, 40, 50. The collected data are each time processed by the read-out circuits until the dose distribution is obtained for the desired measurement positions in the water tank 10, similarly to the case of TPR type dose measurements.

Figure 2:
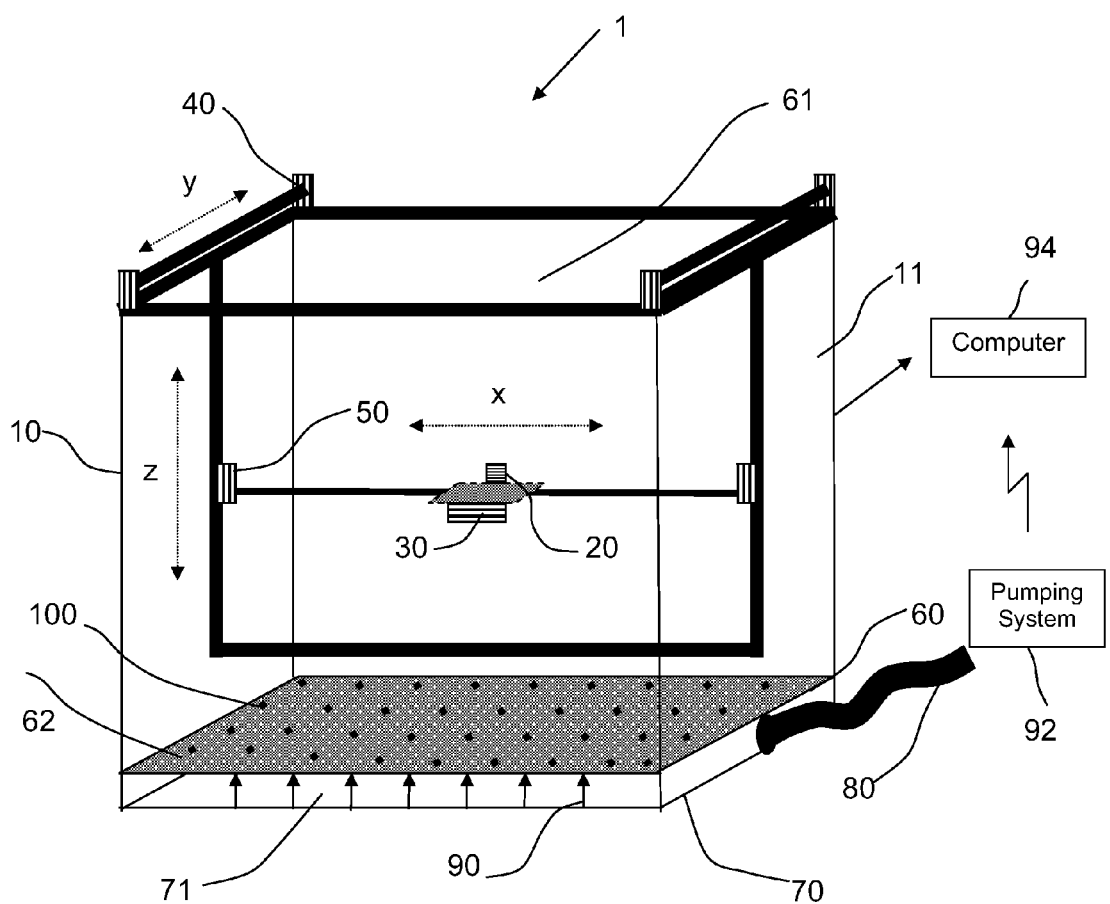
FIG. 2 is a perspective view illustrating a water phantom according to a second embodiment of the invention.

FIG. 2 is a perspective view of a water phantom according to a second embodiment. According to this embodiment the upper base 60 further comprises a detector comprised of a matrix of sensors 100 which are arranged on the surface of the upper base 60 in between the openings 62 in the upper base. In a basic configuration the matrix of sensors is made up of 169 diodes (13×13) evenly distributed over the upper base 60 (spacing between diodes approximately 3.5 cm). In a high-level configuration, the matrix may comprise a higher number of diodes along the central X-, Y-axes, and diagonals of the upper base 60 with a spacing of approximately 0.5 cm in order to measure central axis profiles with a high resolution. According to a variant of this embodiment, the matrix is made up of 1600 ionization chambers and has an active area of 40 cm×40 cm. Each ionization chamber has a diameter of 3.8 mm and a height of 2 mm and is spaced from the others with a pitch of 6.5 mm. This embodiment is particularly advantageous in case of TPR configurations and allows measurements of TPR curves for a two-dimensional matrix of measurement points even during the initial filling of the water phantom 1. However, it is evident that the number, the type and the arrangement of these sensors 100 may vary depending on the particular application without departing from the invention.

Figure 3:
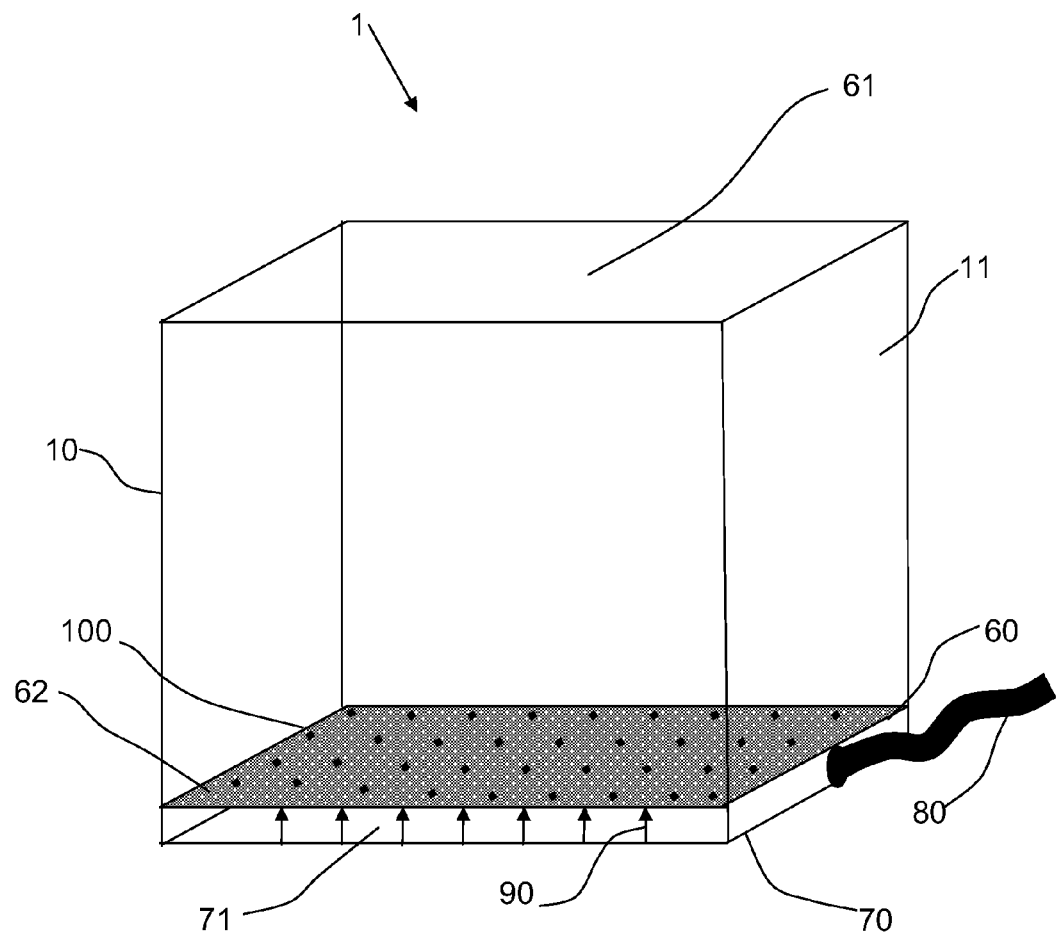
FIG. 3 is a perspective view illustrating a variant of the water phantom of FIG. 2.

FIG. 3 is a perspective view of a water phantom according to a variant of the second embodiment. According to this variant, when the water phantom 1 is used in TPR configuration, the acquisition detector 20 as well as the driving units 30, 40, 50 are not necessary and can be removed from the water phantom. According to this variant, the measurements of TPR curves are provided by the plurality of detectors 100 located in between the openings 62, as above mentioned.

Figure 4:
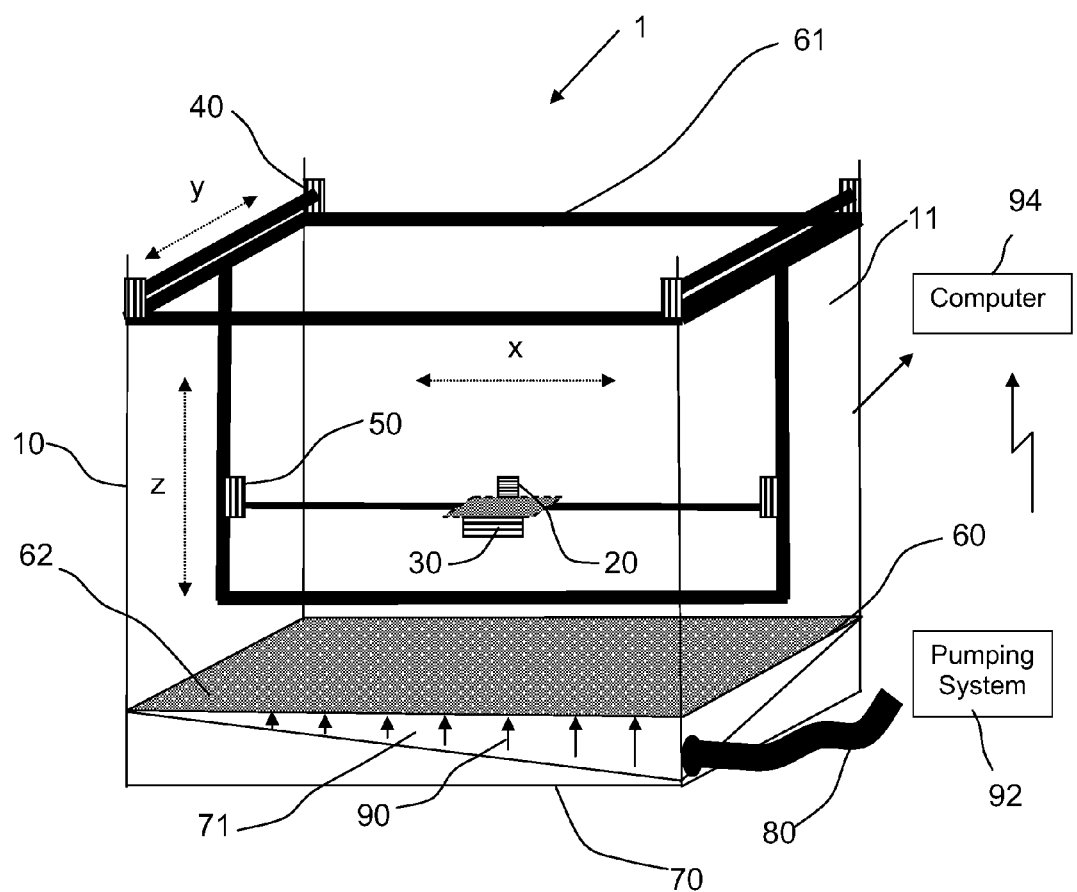
FIG. 4 is a perspective view illustrating a water phantom according to a third embodiment of the invention.

FIG. 4 is a perspective view of a water phantom according to a third embodiment. According to this embodiment, the lower base 70 has an irregular thickness so that the closed lower tank 71 presents a slanted shaped bottom surface having one of the four corners slightly deeper than the others. Since the connection line 80 connecting the pumping system to the closed lower tank 71 is opportunely located near this deeper corner, the presence of this slanted shaped bottom surface ensures that all water can be easily and quickly evacuated from the water tank 10 without having residual water within the water tank which could activate algae growth. It should be noticed that conventional water phantoms typically avoid this problem by manually raising one side of the water tank off the ground or by using expensive water filtration systems. It is evident that the water phantom according to this embodiment is less complex and less expensive with respect to conventional water phantoms.

Figure 5:
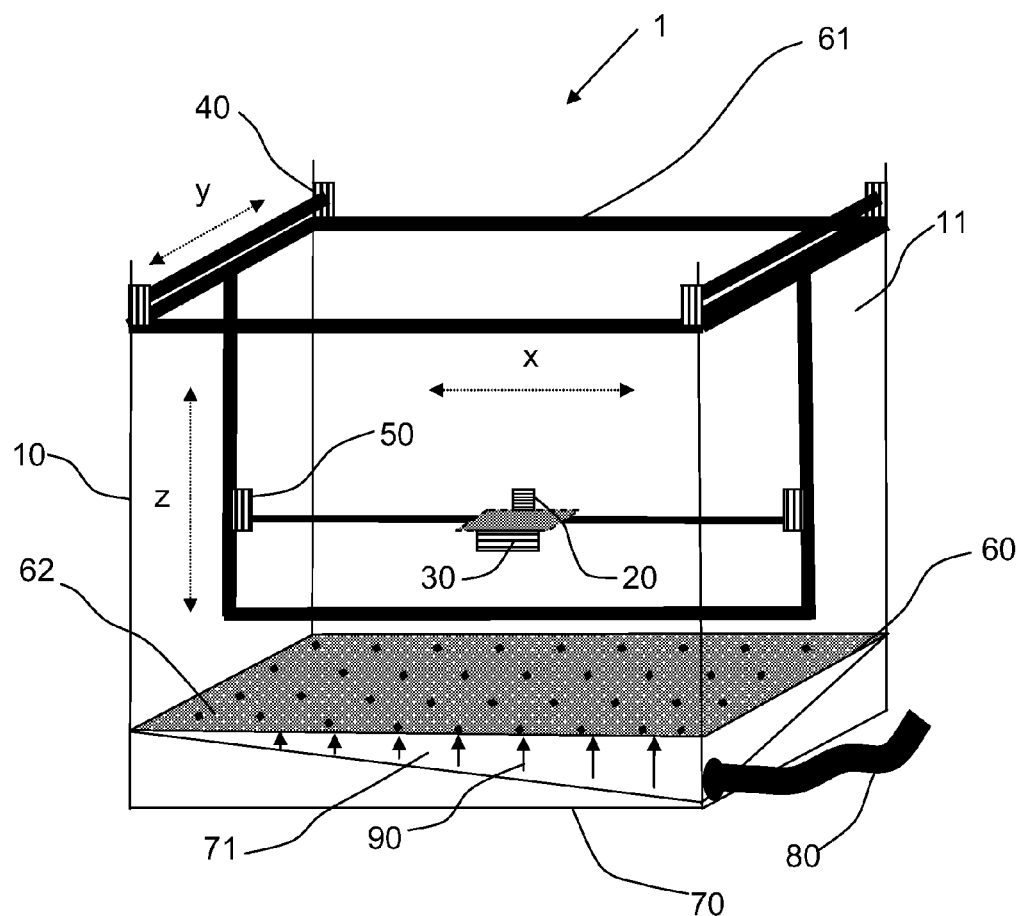
FIG. 5 is a perspective view illustrating a water phantom according to a fourth embodiment of the invention

FIG. 5 is a perspective view of a water phantom according to a fourth embodiment. The water phantom according to this embodiment is similar to that of the third embodiment but additionally comprises a plurality of detectors 100, such as diodes for example, which are arranged in between the openings 62 of the upper base 60.

Figure 6:
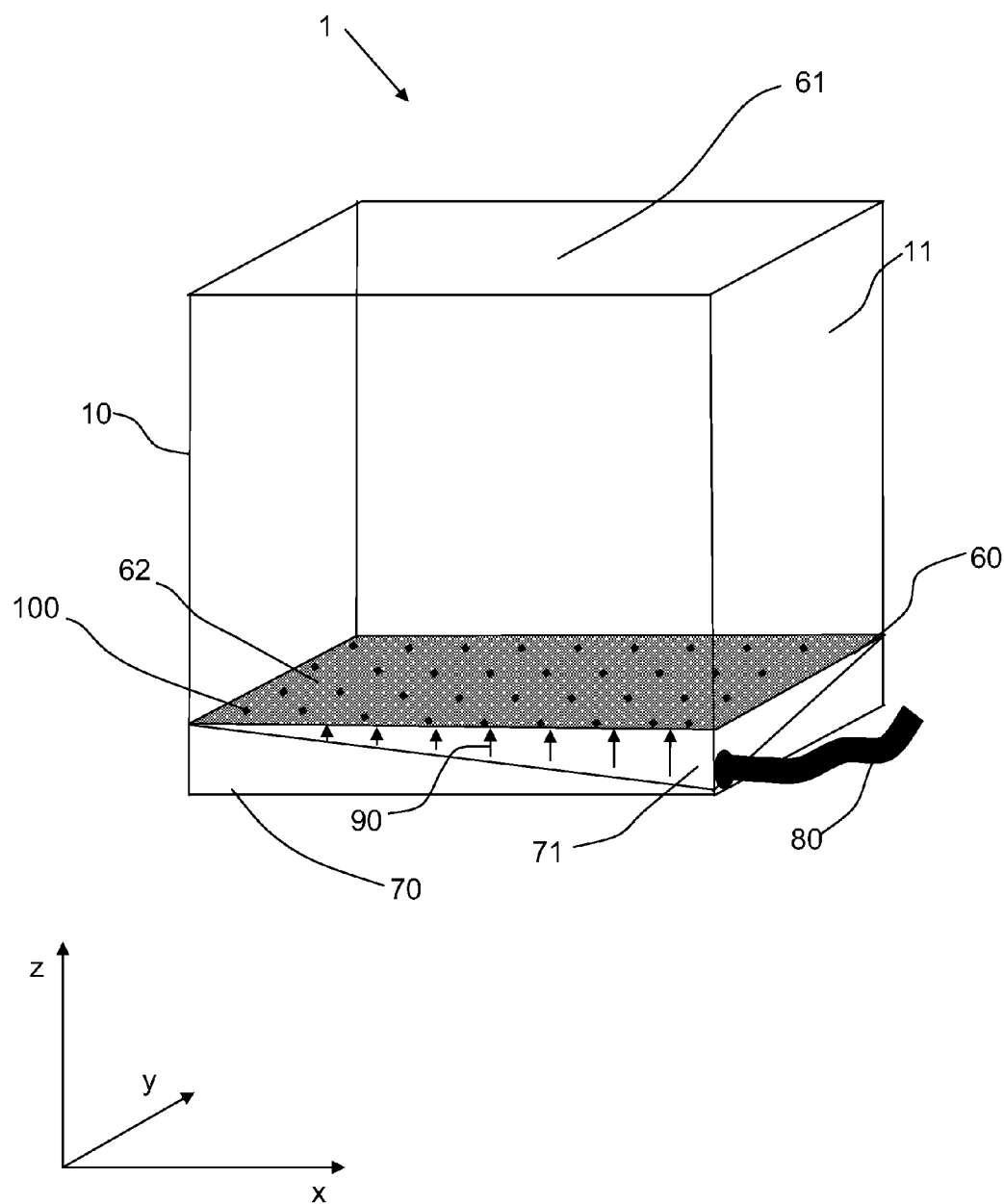
FIG. 6 is a perspective view illustrating a water phantom according to a variant of the water phantom of FIG. 5.

FIG. 6 is a perspective view of a water phantom according to a variant of the fourth embodiment. The water phantom according to this variant is similar to the one represented in FIG. 3 wherein the acquisition detector 20 as well as the driving units 30, 40, 50 are removed and wherein measurements of TPR curves are provided by the plurality of detectors 100 arranged in between the openings 62 of the upper base 60. In this variant the closed lower tank 71 further has a slanted shaped bottom surface having one of the four corners slightly less deep with respect to the others.

The water phantom described herein presents following advantages:

One of the most significant drawbacks of the prior art is the enormous time amount usually required for the commissioning tests, especially when performing measurements in TPR configuration. By using the water phantom, the water phantom described herein can drastically reduce time by providing a water phantom which is configured to be filled with high rate flow pumping systems without creating unwanted waves within the water tank.

Using the water phantom described herein, reduces the amount of time usually required for emptying the water tank and this also prevents unwanted water from remaining within the water tank.

One or more embodiments of the present invention have been described in detail with reference to the attached figures.

It is evident however that the invention is only limited by the claims, since the figures described are only schematic and therefore non-limiting.

In the figures, the size of some of the elements may be exaggerated and not drawn on scale for illustrative purposes. The dimensions and the relative dimensions do not necessarily correspond to actual reductions to practice of the invention. Further, those skilled in the art can recognize numerous variations and modifications of this invention that are encompassed by its scope. Accordingly, the description of preferred embodiments should not be deemed to limit the scope of the present invention.

What is claimed is:

1. A water phantom which measures and determines a dose distribution of radiation produced by a beam selected from the group consisting of a particle beam or photon radiation beam, the water phantom comprising:
   a water tank, the water tank having an upper tank and a lower tank, an upper base between the upper and lower tank, a lower base at a bottom of the lower tank, and side walls, the upper base having an array of a plurality of water admission passages extending through the upper base; and
   a water supply system which supplies water to the water tank, the lower tank configured to be connected to the water supply system to allow a flow of water upward from the lower tank into the upper tank through the array of the plurality of water admission passages in the upper base, the array effective to provide an unturbulent water flow within the upper tank.

2. The water phantom according to claim 1 further comprising an acquisition detector and at least one driving unit, the acquisition detector configured to be moved within the upper tank with the driving unit.

3. The water phantom according to claims 1 or 2 wherein the acquisition detector is a two dimensional detector and the two dimensional detector includes a plurality of sensors located in between the water admission passages, the plurality of sensors effective for simultaneously measuring the dose distribution at a plurality of points in the surface of the upper base.

4. The water phantom according to claim 3, wherein the sensors are selected from the group consisting of ionization chambers; diodes, diode arrays, ionization chamber arrays and combinations thereof.

5. The water phantom according to claim 1 wherein the lower base is downwardly slanted shape to provide a downward inclined portion within the lower tank to a connection with water supply system, the incline configured to allow evacuation of unwanted water from the water tank.

6. A method of measuring and determining the dose distribution of a radiation produced by a particle beam or photon radiation beam using a water phantom comprising:
   a water tank, the water tank having an upper tank and a lower tank, an upper base between the upper and lower tank, a lower base at a bottom of the lower tank, and side walls, the upper base having an array of a plurality of water admission passages extending through the upper base; and
   a water supply system which supplies water to the water tank, the lower tank configured to be connected to the water supply system to allow a flow of water upward from the lower tank into the upper tank through the array of the plurality of water admission passages in the upper base, the array effective to provide an unturbulent water flow within the upper tank;

the method comprising:

moving water from the lower tank to the upper tank through the array of the water admission passages where during the movement of the water from the lower tank to the upper tank the water in the upper tank is not turbulent during the measuring and determining the dose distribution.

7. The method according to claim 6 wherein the method further includes a commissioning of a radiation therapy apparatus.

8. The method according to claims 6 or 7, wherein the method includes performing the measurements are made when the method is practiced on an apparatus in a tissue to phantom ratio configuration.

* * * * *